United States Patent
Rooryck et al.

(10) Patent No.: US 10,052,679 B2
(45) Date of Patent: Aug. 21, 2018

(54) METHOD FOR PRODUCING A HORSESHOE

(71) Applicant: VALUE FEET, Canejan (FR)

(72) Inventors: Thibaut Rooryck, Canejan (FR); Maxime Rooryck, Canejan (FR)

(73) Assignee: VALUE FEET SAS, Canejan (FR)

( * ) Notice: Subject to any disclaimer, the term of this patent is extended or adjusted under 35 U.S.C. 154(b) by 0 days.

(21) Appl. No.: 15/545,086

(22) PCT Filed: Dec. 24, 2015

(86) PCT No.: PCT/FR2015/053753
§ 371 (c)(1),
(2) Date: Jul. 20, 2017

(87) PCT Pub. No.: WO2016/116677
PCT Pub. Date: Jul. 28, 2016

(65) Prior Publication Data
US 2018/0001371 A1    Jan. 4, 2018

(30) Foreign Application Priority Data

Jan. 20, 2015   (FR) .................................. 15 50442

(51) Int. Cl.
*B21K 15/02*    (2006.01)
*A01L 15/00*    (2006.01)
(Continued)

(52) U.S. Cl.
CPC ............. *B21K 15/02* (2013.01); *A01L 11/00* (2013.01); *A01L 15/00* (2013.01); *A61B 5/0077* (2013.01); *A61B 6/508* (2013.01); *A61B 2503/40* (2013.01)

(58) Field of Classification Search
CPC .......... B21K 15/02; A01L 11/00; A01L 15/00; A61B 5/0077; A61B 6/508; A61B 2503/40
(Continued)

(56) References Cited

U.S. PATENT DOCUMENTS 5,319,918 A    6/1994  Baur et al.
6,502,642 B2 *  1/2003  Ahrens .................. A01L 11/00
                                                                          168/45

(Continued)

FOREIGN PATENT DOCUMENTS

EP    0 545 961 A1    6/1993
WO    2010/086190 A1  8/2010

OTHER PUBLICATIONS

International Search Report, dated Mar. 21, 2016, from corresponding PCT/FR2015/053753 application.

*Primary Examiner* — David B Jones
(74) *Attorney, Agent, or Firm* — Young & Thompson

(57) ABSTRACT

Disclosed is a method for producing a horseshoe, wherein the following steps are carried out: a) at least partially viewing the hoof (16) to be shod in order to determine the required measurements for producing a shoe that fits the hoof, b) processing the measurements in order to deduce a provisional shape of the horseshoe, c) recording definitive parameters of the horseshoe, and d) producing the horseshoe on the basis of the definitive parameters. Before step b), the potential existence of at least one area of inflammation and/or at least one area of reduced blood circulation of the foot of the horse, of which the hoof is to receive the shoe, is determined by an infrared detector (17), and in step b), the existence of at least one such area is taken into account in order to determine the provisional shape and/or the structure of the horseshoe.

20 Claims, 1 Drawing Sheet

(51) Int. Cl.
*A61B 5/00* (2006.01)
*A01L 11/00* (2006.01)
*A61B 6/00* (2006.01)

(58) Field of Classification Search
USPC ........................................ 59/61, 66; 168/4, 5
See application file for complete search history.

(56) References Cited

U.S. PATENT DOCUMENTS

| | | | |
|---|---|---|---|
| 7,088,847 B2* | 8/2006 | Craig ..................... | G06K 9/00 168/6 |
| 7,409,818 B2* | 8/2008 | Llewellyn ............... | A01L 11/00 168/4 |
| 7,685,801 B2* | 3/2010 | Brisson .................... | A01L 1/02 168/4 |
| 2014/0231102 A1* | 8/2014 | Moerman ................ | A01L 1/04 168/24 |

\* cited by examiner

METHOD FOR PRODUCING A HORSESHOE

BACKGROUND OF THE INVENTION

Field of the Invention

This invention relates to a method for producing a horseshoe.

This invention further relates to a system for assistance in the production of a horseshoe, for the implementation of this method of manufacturing.

Technological Background

In order to preserve the qualities of the foot of the horse, it is known to protect the foot by placing a horseshoe on the hoof.

Although in the past, the forming of a horseshoe was solely within the competence of the farrier, ordinary shoes are increasingly manufactured in a factory.

Although the horseshoes obtained as such have a shape that is substantially uniform and flat, these shoes allow the farrier to save a non-negligible amount of time.

In order to lighten horseshoes while still providing a suitable resistance, shoes manufactured in a factory are, for competition, typically made from aluminium, and no longer from steel.

However, as such shoes are then difficult to form, the farrier must typically choose a shoe of which the shape and the dimensions are as close as possible to the horseshoe adapted to the hoof to be shod.

Moreover, such shoes cannot take imperfections or pathologies of the hoof into account.

As such, when it is necessary to produce an orthopaedic fitting, the latter is formed by the farrier and is, consequently, in particular made of steel.

Even when this forming can be obtained by reworking a preformed shoe, this operation is particularly long and tedious for the farrier, and in addition, expensive.

Furthermore, an orthopaedic fitting can be suited to correct one or several main problems without treating secondary problems generated by these main problems.

The verification of a painful zone of the foot of the horse by palpation also results in a reaction to the pain of the horse. As it may be necessary to return several times to the painful foot in order to confirm the diagnostic, this verification is especially uncomfortable for the horse. It is furthermore not very precise.

It is also noted that it can be difficult to detect a health problem on the leg or the foot of a horse, for example because there is no apparent clinical sign (subclinical inflammation) or because the infection precedes the appearance of signs of lameness, for example.

It is suitable however to soothe the horse in order to prevent a degradation in the condition of its health.

There is therefore a pressing need for a method that makes it possible to manufacture a horseshoe of which the structure and/or the shape are particularly adapted to the foot of a horse to be shod while still taking its physiological state into account.

OBJECT OF THE INVENTION

This invention aims to overcome the disadvantages of prior art and to respond to the constraints mentioned hereinabove by proposing a method for producing a horseshoe, that is simple in its design and in its operating method, reliable and economical, that makes it possible to determine the parameters of a horseshoe that are best suited for a given foot of a horse while still ensuring that not only the morphology but also any pathologies of this foot are taken into account in such a way as to guarantee optimum comfort for the horse.

Another object of this invention is such a method that is non-invasive and rapid, and therefore not constraining for the horse.

Yet another object of this invention is a system of assistance in the production of a horseshoe, for the implementation of this method for producing a horseshoe.

BRIEF DESCRIPTION OF THE INVENTION

To this effect, the invention relates to a method wherein the following steps are carried out:

a) at least partially viewing the hoof to be shod in order to determine the required measurements for producing a shoe that fits said hoof, b) processing said measurements in order to deduce a provisional shape of the horseshoe, c) recording definitive parameters of said horseshoe, and d) producing said horseshoe on the basis of said definitive parameters.

According to the invention, before the step b), an infrared detector is used to determine the possible existence of at least one area of inflammation and/or of at least one area of reduced blood circulation of the foot of the horse, of which the hoof is intended to receive said shoe, and in step b), the existence of at least one such area is taken into account in order to determine said provisional shape and/or said structure of said horseshoe.

In a known manner, and prior to step a), more preferably, a preparation of the horse is carried out comprising a step of cleaning the hoof, of cutting the horn, etc.

Advantageously, a thermal infrared detector is used to determine the possible existence of at least one area of inflammation and/or of at least one area of reduced blood circulation of the foot of the horse.

A "hot zone" indicates an inflammation or increased circulation of the blood. These hot zones are typically observed in the skin over an injury. A "cold zone" corresponds to a reduction in the blood supply generally due to swelling or the presence of scar tissue.

Detecting these zones non-invasively using infrared thermography advantageously allows for the early diagnosis of a possible pathology in such a way as to adapt the structure and/or the shape of the horseshoe in order to soothe the foot of the horse and not aggravate the condition thereof.

In various particular embodiments of this method, each one has its particular advantages and is liable to undergo many possible technical combinations:

the step of detecting at least one possible area of inflammation and/or area of reduced blood circulation of the foot of the horse is carried out simultaneously when viewing the hoof to be shod.

A thermographic image of the underside of the foot to be shod is as such acquired jointly with the viewing thereof.

As these steps of measuring and of detecting are carried out simultaneously, the time required for developing the shape and/or the structure of the horseshoe is as such drastically reduced by working with two images that supply complementary information.

Advantageously, as these visual and thermal images are obtained with the same line of sight of the underside of the foot of the horse, the information coming from these two images can be superimposed in order to determine the optimum provisional shape of the horseshoe.

in step a), at least one digital image is acquired of at least one portion of the hoof to be shod, at least one radiographic image of said foot is also carried out before the step b) using a portable X-ray source and an X-ray imager in order to determine a possible area of affection.

Of course, when the radiographic image or images reveal the existence of such an affection, this zone is taken into account in step b) in order to determine said provisional shape and/or said structure of said horseshoe.

Such a zone of affection can be linked to a joint affection, lesion, fracture, etc.

before step c), the following steps are carried out: creating a template using the parameters of said horseshoe obtained in step b), placing this template on the hoof to be shod and determining the definitive parameters of said horseshoe to be manufactured.

For the purposes of illustration, this template is obtained using a cutting machine actuated under digital control or a printer such as a digital printer. Entailing for example a simple printing of the provisional shape of the horseshoe on a sheet, the printed sheet is cut in order to obtain the template and position the latter on the hoof in order to provide for the quality thereof or to adjust the parameters thereof.

This template can furthermore be obtained by means of a system for the manufacture of three-dimensional objects, and in particular a three-dimensional printer, such as a thermal printer for the manufacture of a three-dimensional model by sequential deposit of a plurality of cross-section layers.

Thanks to the production of this template in the presence of the horse, the determination of the correct set of parameters and of the final quality of the horseshoe that will be produced using the set of final parameters is thus assured, directly.

the step b) comprises a step of correcting the parameters of the horseshoe corresponding to at least an adjustment of the external curve, or of the contour, of the horseshoe.

The particularities of the manufacture of the horseshoe determined by the farrier are as such taken into account. Purely for the purposes of information, this may be the taking into account of the deformation of the hoof when it is bearing against the ground.

the foot of the horse having at least one painful area or an area of reduced blood circulation, in step b) the structure of the shoe is lightened in line with said at least one area is such a way as to soothe the latter, in step d), at least one portion of the horseshoe is carried out by a method of manufacturing by three-dimensional printing.

Purely for the purposes of illustration, as the horseshoe has a multilayer structure, at least one of these layers is obtained by a method of manufacture via three-dimensional printing then the layer obtained as such is assembled to at least two other layers, for example by gluing, in order to form the horseshoe.

The layer obtained can be made of metal (Aluminium, iron, titanium, etc.) or of polymer.

For example, it can be obtained using an agglomerating metal powder, also called "sinterable powder".

the outer surface of said shoe is marked with a unique identifier of said horseshoe and possibly an identifier of the foot of the horse to be shod for which said horseshoe is intended.

This unique identifier comprises a sign obtained by the reaction of the material that comprises said external surface of the horseshoe with a chemical substance or the application of a source of heat such as a laser beam.

This sign can have a surface relief such as at least one hollow.

Preferably, this sign comprises a vertical line, a slanted line, one or several circles, one or several digits, one or several letters, a barcode, a symbol and combinations of these elements.

a finish of the colour of the horseshoe obtained as such is carried out by treatment of at least a portion of the outer surface of said shoe, said treatment comprising a step of anodising and a step of coloration, or by depositing on at least one portion of the outer surface of said shoe a decorative coating having a determined colour.

Purely for the purposes of illustration, the coloration of this surface can be carried out using a method of coloration via adsorption, an electrolytic method of coloration, a method of coloration via interference or any combination of these methods.

Alternatively, after having anodised the external surface of the horseshoe, this portion can be exposed to a method of cold or hot plugging such as by immersing this portion in deionised water, at a temperature of about 90° C. to 100° C., a colouring agent such as methylene blue for example which will give the horseshoe a blue colour.

By way of example, the electrolytic method of coloration comprises the electrolytic deposition of particles of a solution of metal salt on pores of an oxide layer of the surface of the shoe.

depositing a wear-resistant decorative coating, a precious metal is chosen from the group comprising Gold, Silver, Platinum, Palladium, Rhodium, Iridium, Osmium, Rhenium, Ruthenium and/or an alloy of one of these metals with one or several other metals.

Purely for the purposes of illustration, a base layer comprised of a precious metal alloy is deposited galvanically.

In addition, in order to reinforce the resistance of gold plating for example, a surface layer of a gold alloy that has a purity greater than or equal to 22 carats for example can be deposited galvanically.

Alternatively, in order to carry out this golden colour decorative coating which is resistant to wear and tear, during a first step, on the surface of the horseshoe, at least a first layer of titanium nitride is deposited, then during a second step, this first layer is activated by ionic bombardment in a vacuum in such a way that it is able to receive, afterwards a layer of gold or of a gold alloy with a high degree of purity, deposited via the galvanic method, with the definitive colour desired. During this second step, at least partially simultaneously a second thin layer of gold and/or of a gold alloy is deposited. This deposition of gold atoms is carried out in a vacuum via evaporation, by ion projection or by cathode sputtering, while still continuing with an ionic bombardment of the titanium nitride surface. During this second step, the power of this ion bombardment is reduced progressively.

The gold alloy is, preferably, with a high number of carats, for example a gold alloy with at least 22 carats comprising, as an alloy element, Indium, Nickel, Cobalt, Cadmium, Copper, Silver, Palladium, Zinc or Antimony.

This invention further relates to a system for assistance in the production of a horseshoe, for the implementation of the method such as described hereinabove.

According to the invention, this system comprises:
an optical device,
an infrared detector, with said system being arranged in such a way that at least said optical device views the portion of said hoof intended to receive said horseshoe, and means providing for the transfer of the data acquired by said infrared detector and said optical device to a storage unit or a means for processing this data.

Preferably, this optical device is a digital camera. The latter can as such comprise an array of CCD sensors.

Advantageously, the signals emitted by the sensor or sensors of the optical device are wireless communication signals. Preferably, the same applies for the signals emitted by the sensor or sensors of the infrared detector.

These wireless communication signals can be based on the following protocols: IEEE 802.11 b/g/n (Wi-Fi), IEEE 802.15.1 (Bluetooth) or GSM or GPRS.

Alternatively, these signals are transmitted via a wired network (electrical, telephone, Ethernet) in order to prevent potential disturbances.

The system advantageously includes a means for processing these signals comprising a calculation unit, a keyboard, a display screen and a storage unit for storing data sets that correspond to different shoes. On this calculation unit, are executed one or several pieces of data processing software in order to process the signals received from the sensor or sensors of the optical device and from the infrared detector and store them.

In various particular embodiments of this system, with each one having its particular advantages and able to undergo many possible technical combinations:

this system comprises an input element transparent to visible light and in an infrared range, said input element being carried by a cover and intended to receive as support or be placed in the vicinity of said hoof to be shod, with said cover carrying said optical device and said infrared detector that is sensitive in the infrared range.

this system comprises a deflecting element that reflects the incident radiation in said infrared band to said infrared detector, said deflecting element being carried by said cover, said deflecting element being transparent in the visible range.

Alternatively, this system comprises a deflecting element that reflects the incident radiation in the visible range, said deflecting element being carried by said cover, said deflecting element being transparent in said infrared band.

By way of example, this can be an interference filter formed of several layers that have a high transparency for the visible light range and a high reflective power for the infrared radiation in said infrared band.

Alternatively, this system can comprise a system for the optical deflection and offsetting of images defining the same line of sight for said infrared detector and said optical device. This line of sight is more preferably perpendicular or substantially perpendicular to said input element.

Page 8 The system therefore advantageously comprises an optical channel with an input that is shared with the infrared detector and the optical device.

the optical device is placed at a distance from the input element such as a transparent window, in order to view said hoof to be shod from underneath.

The optical axis of the optical device is for example perpendicular to the input element.

the system comprises an optical device that is sensitive to infrared and an infrared filter in order to allow to pass only the infrared beyond a predetermined cut-off frequency or a computer program configured to process the images acquired by said optical device sensitive to infrared and supply data only in the infrared range.

The optical axis of this optical device sensitive to the visible light range and to infrared, can then be positioned normally, or substantially normally, to the plane defined by the input element, transparent in the visible light range and in an infrared band. The obtaining of images in the infrared range is then obtained either by positioning an IR filter in front of the optical device, with this IR filter allowing to pass only infrared beyond a predefined cut-off frequency, for example 720 nm, or by processing the data acquired by the optical device by means of software configured to provide infrared images. The system for assistance then comprises a single optical device, which is also used as an infrared detector.

said cover comprises a means for displaying that makes it possible to display said hoof to be shod such as viewed by the optical device and/or said infrared detector after conversion into a video signal in an electronic processing circuit.

the system comprises a computer-controlled cutter, a means for printing or a system for the manufacture of three-dimensional objects, making it possible to carry out a template for a horseshoe using parameters determined beforehand.

This system can as such comprise a digital or three-dimensional printer.

said infrared detector is a thermal infrared detector.

This detector comprises for example an array of sensors such as microbolometers that advantageously do not require cooling.

Purely for the purposes of illustration, such sensors can operate in the 8 to 14 μm band.

More generally, this invention also relates to a method for producing a horseshoe wherein at least the following steps are carried out:

a) at least partially viewing the hoof to be shod in order to determine the required measurements for producing a shoe that fits said hoof, b) processing said measurements in order to deduce therefrom a provisional shape of the horseshoe, c) recording definitive parameters of said horseshoe, and d) producing said horseshoe on the basis of said definitive parameters.

According to the invention, in step d), the horseshoe is produced by a method of manufacture via three-dimensional printing.

The three-dimensional printing (3D) can be carried out through 3D printing with the deposition of melted material, or by 3D printing via powder binding, or encore par photo polymerisation.

Preferably, a metal powder such as steel, platinum or aluminium, is used as a base material to form the horseshoe via three-dimensional printing.

Advantageously, it is as such possible, after having determined the definitive parameters of the horseshoe, to produce the latter directly. A significant reduction in the delays for production and the possibility of shodding the horse on site are as such obtained.

Such a method of three-dimensional printing that makes it possible to create parts with complex geometries, is also particularly suited to the production of orthopaedic shoes which can have geometries that are difficult for a farrier to produce.

The system for assistance in the production of a horseshoe, for the implementation of the method such as described hereinabove then comprises an optical device, an infrared detector, with said system being arranged in such a way that at least said optical device views the portion of said hoof intended to receive said horseshoe, means providing for the transfer of the data acquired by said infrared detector and said optical device to a storage unit or a means for processing this data, and a three-dimensional printing machine.

The three-dimensional printing machine is then connected to the means of data processing such as a computer. The latter then comprises a computer program configured to control this printing machine in order to carry out the horseshoe using the definitive parameters of the latter.

This system for assistance is advantageously installed in a machine that can either be towed or be self-propelled. For example, this can be a motorised vehicle in such a way that the operator can travel directly as close as possible to the location where the horse to be shod is located.

BRIEF DESCRIPTION OF THE DRAWINGS

Other advantages, purposes and particular characteristics of this invention shall result from the following description, provided for the purposes of explanation and in no way limiting, with respect to the annexed drawings, wherein.

DETAILED DESCRIPTION OF EMBODIMENT OF THE INVENTION

Firstly, note that the figures are not to scale.

Figure 1:
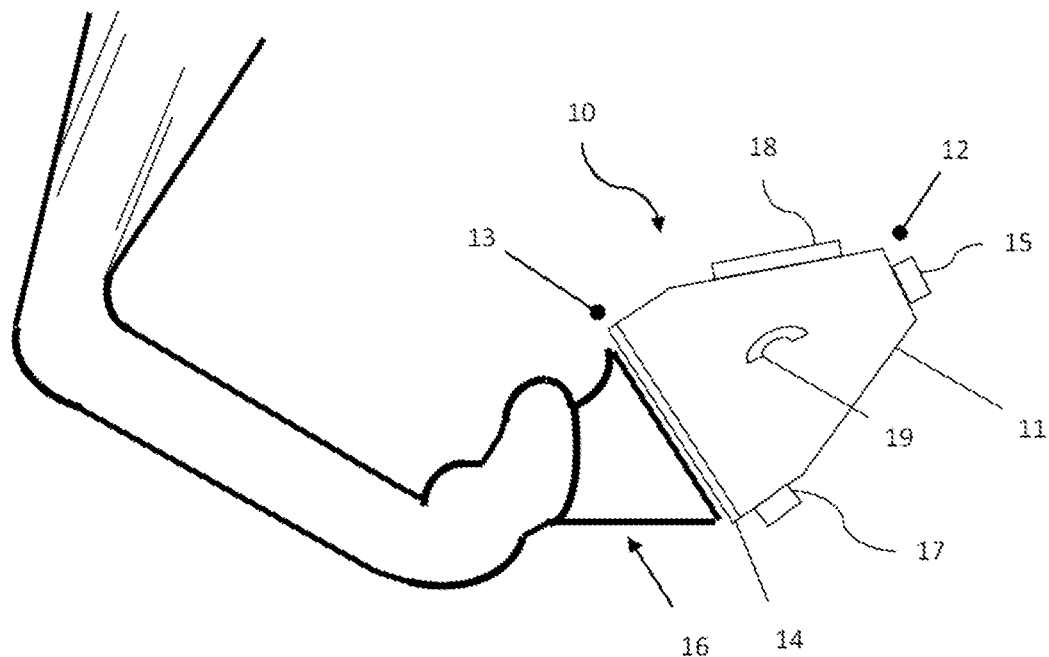
FIG. 1 diagrammatically shows a side view of a unit for assistance in determining the parameters of a horseshoe according to a particular embodiment of this invention, with the foot of a horse being placed against the transparent window placed at the inlet of this unit.

FIG. 1 diagrammatically shows a side view of a unit for assistance in determining parameters of a horseshoe according to a particular embodiment of this invention.

This ensemble 10 comprises a cover 11 of extended shape and with a flared shape starting from a rear end 12 towards its front end 13.

The front end 13 of this cover which defines the inlet channel of this unit 10, is of cylindrical shape.

At the inlet of this unit 10, the cover 11 carries a window 14 that is transparent to the visible light range and to infrared radiation in an infrared band, for example to infrared radiation up to 12 μm.

Advantageously, this transparent window 14 carries a grid pattern that facilitates the measurements of the hoof and, consequently, the determining of the parameters of the horseshoe.

The rear portion of the cover 11 carries a digital camera 15 in order to observe the underside through the window 14, the foot 16 of the horse received bearing against this transparent window 14. The aiming axis of the digital camera is perpendicular or substantially perpendicular to this window 14. Solely for the purposes of illustration, this digital camera comprises an array of CCD sensors.

The invention then provides the processing of the images obtained, by a computer program executed on a calculation unit (not shown) in order to be able to calculate the characteristics of the hoof to be shod and, consequently, determine using these characteristics, the measurements (external curvature, size and width of the bearing surface (i.e. coverage), clip, hole outer edge, hole inner edge, rolling, etc.) of the horseshoe suited for this hoof.

On this calculation unit, are also stored one or several data sets that make it possible, for example, once the measurements of the horseshoe are determined, to propose to the user one or several horseshoe models that can be suitable for the hoof to be shod.

By way of example, these horseshoe models vary according to the perspective for use under consideration, and discipline, of the horse (leisure, trot, racing, polo, etc.), of its race, of its age, of any climatic conditions (ice, snow, etc.), orthopaedic problems, etc. . . . so as to maintain or optimise the locomotive performance of the horse. The final shape of the horseshoe is determined by the farrier and/or the veterinarian.

The cover 11 of this unit 10 also carries a thermal infrared detector 17 in order to obtain thermographic images of the foot 16 of the horse.

These images processed by a suitable software executed on the calculation unit allow the user to detect one or several physiological problems (inflammation, lesion, reduced blood circulation, etc.) in the foot of the horse and to take this problem or these problems into account in the final definition (shape and/or structure) of the horseshoe.

Possibly, the inlet of this unit 10 also comprises a filter (not shown) that is transparent solely in the infrared band to which this infrared detector 17 is sensitive. This filter is mobile in order to be able to be separated or positioned with respect to this transparent window 14.

The cover 11 carries a deflecting element (not shown) that reflects the incident radiation in said infrared band towards the infrared detector 17, with this deflecting element being transparent in the visible range.

The digital camera 15 and the infrared detector 17 are each connected via a suitable cable (not shown) to the calculation unit in order to transmit the signals emitted by their respective sensors.

The external surface of the cover 11 also receives a visualisation screen 18 which makes it possible to display a live image of the hoof to be shod such as observed by the digital camera and/or imaged by said infrared detector after conversion into a video signal in an electronic processing circuit (not shown).

The cover 11 advantageously comprises handles 19 that allow for each manipulation of the unit 10 by the user.

The cover 11 can also comprise a threaded orifice intended to cooperate with a tripod (not shown) in order to provide the support for the unit 10 in fixed position.

Figure 2:
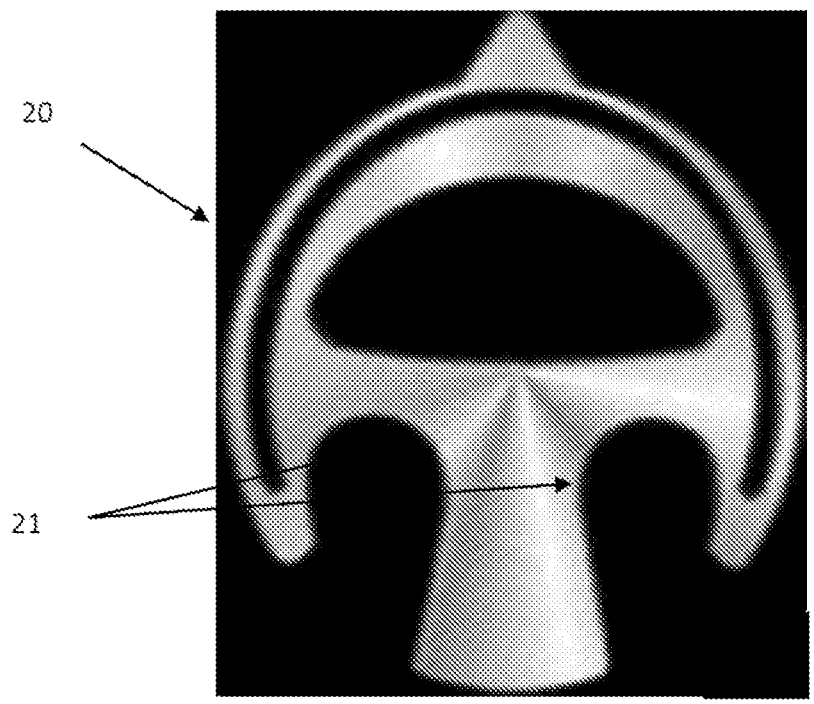
FIG. 2 is a front view of an orthopaedic fitting obtained by the method of the invention according to a particular embodiment.

FIG. 2 is a front view of an orthopaedic fitting obtained by the method of the invention according to a particular embodiment.

The invention claimed is:

1. Method for producing a horseshoe, wherein the following steps are carried out:
    a) at least partially viewing the hoof (16) to be shod in order to determine the required measurements for producing a shoe that fits said hoof (16),
    b) processing said measurements in order to deduce a provisional shape of the horseshoe,
    c) recording definitive parameters of said horseshoe, and
    d) producing said horseshoe on the basis of said definitive parameters, wherein
        before the step b), an infrared detector (17) is used to determine the possible existence of at least one area of inflammation and/or of at least one area of reduced blood circulation of the foot of the horse, of which the hoof (16) is intended to receive said shoe, and in step b), the existence of at least one such area is taken into account in order to determine said provisional shape and/or said structure of said horseshoe.

2. Method according to claim 1, wherein the step of detecting at least one possible area of inflammation and/or area of reduced blood circulation of the foot of the horse is carried out simultaneously when viewing the hoof (16) to be shod.

3. Method according to claim 1, wherein in step a), at least one digital image is acquired of at least one portion of the hoof (16) to be shod.

4. Method according to claim 1, wherein at least one radiographic image of said foot is also carried out before the step b) using a portable X-ray source and an X-ray imager in order to determine a possible area of affection.

5. Method according to claim 1, wherein before step c), the following steps are carried out: creating a template using the parameters of said horseshoe obtained in step b), placing this template on the hoof (16) to be shod and determining the definitive parameters of said horseshoe to be manufactured.

6. Method according to claim 1, wherein step b) comprises a step of correcting the parameters of the horseshoe corresponding to at least an adjustment of the external curve of the horseshoe.

7. Method according to claim 1, wherein the foot of the horse having at least one painful area or an area of reduced blood circulation, in step b) the structure of the shoe is lightened in line with said at least one area is such a way as to soothe the latter.

8. Method according to claim 1, wherein in step d), at least one portion of the horseshoe is carried out by a method of manufacturing by three-dimensional printing.

9. Method according to claim 1, wherein the outer surface of said shoe is marked with a unique identifier of said horseshoe and possibly an identifier of the foot of the horse to be shod for which said horseshoe is intended.

10. Method according to claim 1, wherein a finish of the colour of the horseshoe obtained as such is carried out by treatment of at least a portion of the outer surface of said shoe, said treatment comprising a step of anodising and a step of coloration, or by depositing on at least one portion of the outer surface of said shoe a decorative coating having a determined colour.

11. Method according to claim 10, wherein depositing a wear-resistant decorative coating, a precious metal is chosen from the group comprising Gold, Silver, Platinum, Palladium, Rhodium, Iridium, Osmium, Rhenium, Ruthenium and/or an alloy of one of these metals with one or several other metals.

12. System for assistance in carrying out a horseshoe, for the implementation of the method according to claim 1, further comprising:
an optical device (15),
an infrared detector (17),
with said system being arranged in such a way that at least said optical device (15) views the portion of said hoof (16) intended to receive said horseshoe, and
means providing for the transfer of the data acquired by said infrared detector (17) and said optical device (15) to a storage unit or a means for processing this data.

13. System according to claim 12, further comprising an input element transparent to visible light and in an infrared range carried by a cover, said input element being intended to receive as support or be placed in the vicinity of said hoof (16) to be shod, with said cover carrying said optical device (15) and said infrared detector (17) that is sensitive in the infrared range.

14. System according to claim 12, further comprising an optical device that is sensitive to infrared and an infrared filter in order to allow to pass only the infrared beyond a predetermined cut-off frequency or a computer program configured to process the images acquired by said optical device sensitive to infrared and supply data only in the infrared range.

15. System according to claim 13, wherein said cover comprises a means for displaying (18) that makes it possible to display said hoof (16) to be shod such as viewed by the optical device (15) and/or said infrared detector (17) after conversion into a video signal in an electronic processing circuit.

16. System according to claim 12, further comprising a computer-controlled cutter, a means for printing or a system for the manufacture of three-dimensional objects, making it possible to carry out a template for a horseshoe using parameter determined beforehand.

17. Method according to claim 2, wherein in step a), at least one digital image is acquired of at least one portion of the hoof (16) to be shod.

18. Method according to claim 2, wherein at least one radiographic image of said foot is also carried out before the step b) using a portable X-ray source and an X-ray imager in order to determine a possible area of affection.

19. Method according to claim 3, wherein at least one radiographic image of said foot is also carried out before the step b) using a portable X-ray source and an X-ray imager in order to determine a possible area of affection.

20. Method according to claim 2, wherein before step c), the following steps are carried out: creating a template using the parameters of said horseshoe obtained in step b), placing this template on the hoof (16) to be shod and determining the definitive parameters of said horseshoe to be manufactured.

* * * * *